(12) United States Patent
Halford et al.

(10) Patent No.: US 10,314,326 B2
(45) Date of Patent: *Jun. 11, 2019

(54) COMPOSITION FOR REDUCING FOOD INTAKE

(71) Applicant: Natures Remedies Ltd, Cambridge (GB)

(72) Inventors: Jason Christian Grovenor Halford, Manchester (GB); Trevor Rodney Jarman, Bucks (GB)

(73) Assignee: NATURES REMEDIES LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,828

(22) Filed: Oct. 6, 2017

(65) Prior Publication Data

US 2018/0027860 A1    Feb. 1, 2018

Related U.S. Application Data

(63) Continuation-in-part of application No. 14/989,182, filed on Jan. 6, 2016, now Pat. No. 9,789,151, which is a continuation-in-part of application No. 12/824,509, filed on Jun. 28, 2010, now abandoned.

(60) Provisional application No. 61/222,141, filed on Jul. 1, 2009.

(51) Int. Cl.
| | |
|---|---|
| *A23L 33/10* | (2016.01) |
| *A23L 33/21* | (2016.01) |
| *A23L 33/00* | (2016.01) |
| *A61K 36/28* | (2006.01) |
| *A61K 36/77* | (2006.01) |
| *A23L 33/105* | (2016.01) |
| *A61K 31/733* | (2006.01) |
| *A61K 36/185* | (2006.01) |
| *A61K 31/4412* | (2006.01) |
| *A23L 33/15* | (2016.01) |
| *A23C 9/133* | (2006.01) |
| *A23C 9/152* | (2006.01) |
| *A61K 31/675* | (2006.01) |
| *A61K 31/395* | (2006.01) |
| *A61K 31/375* | (2006.01) |

(52) U.S. Cl.
CPC ............ *A23L 33/105* (2016.08); *A23C 9/133* (2013.01); *A23C 9/152* (2013.01); *A23L 33/10* (2016.08); *A23L 33/15* (2016.08); *A23L 33/21* (2016.08); *A23L 33/30* (2016.08); *A61K 31/375* (2013.01); *A61K 31/395* (2013.01); *A61K 31/4412* (2013.01); *A61K 31/675* (2013.01); *A61K 31/733* (2013.01); *A61K 36/185* (2013.01); *A61K 36/28* (2013.01); *A61K 36/77* (2013.01); *A23V 2002/00* (2013.01); *A23V 2200/30* (2013.01); *A23V 2250/21* (2013.01)

(58) Field of Classification Search
CPC .... A61K 36/185; A61K 36/77; A61K 31/375; A61K 31/395; A61K 31/4412; A61K 31/675; A61K 31/733; A61K 36/28; A61K 2300/00; C12P 19/04; C12R 1/38; A23L 33/10; A23L 33/105; A23L 33/15; A23V 2002/00; Y10S 435/813; Y10S 435/831; Y10S 435/874
See application file for complete search history.

(56) References Cited

U.S. PATENT DOCUMENTS

| | | | |
|---|---|---|---|
| 5,945,107 A | 8/1999 | Hessel et al. | 424/728 |
| 8,470,377 B2 | 6/2013 | Halford et al. | 424/725 |
| 9,789,151 B2 * | 10/2017 | Halford | A61K 36/77 |
| 2004/0087514 A1 | 5/2004 | Hughes et al. | 514/23 |
| 2004/0198754 A1 | 10/2004 | McKee et al. | 514/263.34 |
| 2004/0265398 A1 | 12/2004 | Fleischner | 424/725 |
| 2005/0238654 A1 | 10/2005 | Takeda | 424/195.15 |
| 2006/0083795 A1 | 4/2006 | Shatkina et al. | 424/725 |
| 2006/0228412 A1 | 10/2006 | Clouatre et al. | 424/466 |
| 2008/0081826 A1 | 4/2008 | Springuel et al. | 514/326 |
| 2008/0305096 A1 | 12/2008 | Verdegem et al. | 424/94.4 |
| 2014/0322370 A1 | 10/2014 | Jarman et al. | 424/774 |

FOREIGN PATENT DOCUMENTS

| | | |
|---|---|---|
| AU | 2006/100120 A4 | 2/2006 |
| EP | 1037644 | 3/2004 |
| WO | WO99/29333 | 6/1999 |
| WO | WO 2004/082609 A2 | 9/2004 |
| WO | WO 2005/034650 A1 | 4/2005 |

OTHER PUBLICATIONS

Ruxton (Efficacy of Zotrim: A Herbal Weight Loss Preparation Nutr. & Food Sci., 34(1), 2004. pp. 25-28), (Year: 2004).*
Natural Alternative Products (NAP) (<natural-alternative-products.co.uk/zotrim-180tablets-p-642.html>, Jul. 2007, accessed Jan. 8, 2012, 2 pp.) (Year: 2007).*
Harold JA, et al "Acute effects of a herb extract formulation and inulin fibre on appetite, energy intake and food choice" Appetite, Mar. 1, 2013 (ePub Dec. 1, 2012),62,pp. 84-90; doi:10.1016/j.appet.2012.11.018. (Year: 2012).*
Zotrim "Introducing Zotrim Plus" 2017, <URL:https://zotrim.com/zotrim-plus> , 6 pages. (Year: 2017).*
Andersen, T. and Fogh, J. "Weight Loss and Delayed Gastric Emptying Following a South American Herbal Preparation in Overweight Patients" Journal of Human Nutrition and Dietetics 2001 14:243-250.

(Continued)

*Primary Examiner* — Aaron J Kosar
(74) *Attorney, Agent, or Firm* — Licata & Tyrrell P.C.

(57) ABSTRACT

The present invention features a composition and method for suppressing appetite. The composition of the invention is composed of yerbe maté extract, guarana extract, and damiana extract in combination with a dietary fiber.

2 Claims, No Drawings

(56) References Cited

OTHER PUBLICATIONS

Bianchi, M. and Capurso, L. "Effects of Guar Gum, Ispaghula and Microcrystalline Cellulose on Abdominal Symptoms, Gastric Emptying, Orocaecal Transit Time and Gas Production in Health Volunteers" Digestive and Liver Disease 2002 34 (Supplement 1):S129-S133.

Bosch et al. "The Effects of Dietary Fibre Type on Satiety-Related Homrones and Voluntary Food Intake in Dogs" British Journal of Nutrition 2009 102:318-325.

Burton-Freeman, B. "Dietary Fiber and Energy Regulation" The Journal of Nutrition 2000 130:272S-275S.

Gerken et al. "The Obesity-Associated FTO Gene Encodes a 2-Oxoglutarate-Dependent Nucleic Acid Demethylase" Science 2007 318:1469-1472.

Guarner, F. "Inulin and Oligofructose: Impact on Intestinal Diseases and Disorders" British Journal of Nutrition 2005 93:S61-S65.

Hellström et al. "GLP-1 Suppresses Gastrointestinal Motility and Inhibits the Migrating Motor Complex in Healthy Subjects and Patients with Irritable Bowel Syndrome" Neurogastroenterology and Motility 2008 20:649-659.

Jerlhag et al. "Ghrelin Administration into Tegmental Areas Stimulates Locomotor Activity and Increases Extracellular Concentration of Dopamine in the Nucleus Accumbens" Addiction Biology 2006 12:6-16.

Kim et al. Sensory Properties of Barley; CFW Report; Cereal Foods World; Sep./Oct. 2005; 50, 5. pp. 271-277.

Mason, P. "(1) OTC Weight Control Products" The Pharmaceutical Journal 2002 269(7206):103-105.

Meier et al. "Glucagon-like Peptide 1 as a Regulator of Food Intake and Body Weight: Therapeutic Perspectives" Europen Journal of Pharmacology 2002 440:269-279.

Ørskov et al. "Complete Sequences of Glucagon-Like Peptide-1 from Human and Pig Small Intestine" The Journal of Biological Chemistry 1989 264(22):12826-12829.

Piche et al. "Colonic Fermentation Influences Lower Esophageal Sphincter Function in Gastroesophageal Reflux Disease" Gastroenterology 2003 124:894-902.

Ruxton, C.H.S. "Efficacy of Zotrim: a Herbal Weight Loss Preparation" Nutrition and Food Science 2004 34(1):25-28.

Ruxton, C.H.S. and Gardner, E.J. "A Review of the Efficacy and Safety of Key Ingredients of Over-the-Counter Products for Weight Management" British Food Journal 2006 107(2):111-125.

Ruxton et al. "Effects of an Over-the-Counter Herbal Weight Management Product (Zotrim®) on Weight and Waist Circumference in a Sample of Overweight Women: a Consumer Study" Nutrition and Food Science 2005 35(5):303-314.

Ruxton et al. "Effectiveness of a Herbal Supplement (Zotrim™) for Weight Management" British Food Journal 2007 109(6):416-428.

Schjoldager et al. "GLP-1 (Glucagon-like Peptide 1) and Truncated GLP-1, Fragments of Human Proglucagon, Inhibit Gastric Acid Secretion in Humans" Digestive Diseases and Sciences 1989 34:703-708.

Vinik, A.I. and Jenkins, D.J. "Dietary Fiber in Management of Diabetes" Diabetes Care 1988 11(2):160-173.

Zander et al. "Effect of 6-Week Course of Glucagon-like Peptide 1 on Glycaemic Control, Insulin Sensitivity, and β-Cell Function in Type 2 Diabetes: a Parallel-group Study" The Lancet 2002 359:824-830.

Natural Alternative Products (NPA); online, URL <www.natural-alternative-products.co.uk/zotrim-180tablets-p-642.html, accessed Jan. 8, 2012, 2 pages (Jul. 2007).

Office Communication dated Nov. 4, 2011 from U.S. Appl. No. 12/824,509, filed Jun. 28, 2010.

Office Communication dated Feb. 23, 2012 from U.S. Appl. No. 12/824,509, filed Jun. 28, 2010.

Office Communication dated May 31, 2012 from U.S. Appl. No. 12/824,509, filed Jun. 28, 2010.

Office Communication dated Nov. 21, 2012 from U.S. Appl. No. 12/824,509, filed Jun. 28, 2010.

Office Communication dated Sep. 10, 2013 from U.S. Appl. No. 12/824,509, filed Jun. 28, 2010.

Office Communication dated Oct. 17, 2013 from U.S. Appl. No. 12/824,509, filed Jun. 28, 2010.

Office Communication dated Dec. 18, 2013 from U.S. Appl. No. 12/824,509, filed Jun. 28, 2010.

Office Communication dated Nov. 20, 2014 from U.S. Appl. No. 12/824,509, filed Jun. 28, 2010.

Office Communication dated Jul. 7, 2015 from U.S. Appl. No. 12/824,509, filed Jun. 28, 2010.

Office Communication dated Dec. 18, 2015 from U.S. Appl. No. 12/824,509, filed Jun. 28, 2010.

Office Communication dated May 13, 2013 from U.S. Appl. No. 13/380,099, filed Jan. 25, 2012.

International Search Report from PCT/IB2010/001722, dated Mar. 28, 2011.

International Preliminary Report on Patentability from PCT/IB2010/001722, dated Dec. 19, 2011.

Office Communication dated Dec. 22, 2016 from U.S. Appl. No. 14/989,182, filed Jan. 6, 2016.

Office Communication dated Jun. 22, 2017 from U.S. Appl. No. 14/989,182, filed Jan. 6, 2016.

Office Communication dated Jul. 19, 2017 from U.S. Appl. No. 14/989,182, filed Jan. 6, 2016.

Office Communication dated Aug. 1, 2017 from U.S. Appl. No. 14/989,182, filed Jan. 6, 2016.

Harrold et al. "Acute effects of a herb extract formulation and inulin fibre on appetite, energy intake and food choice" Appetite 2013 62:84-90.

Zotrim "Introducing Zotrim Pluz" 2017 URL:https://zotrim.com/zotrim-plus , 6 pages.

Zotrim "Nutritional Information" (Zotrim & Zotrim Plus Labels) 2017 URL:https://zotrim.com/nutritional-information, 3 pages.

* cited by examiner

COMPOSITION FOR REDUCING FOOD INTAKE

INTRODUCTION

This application is a continuation-in-part application of U.S. application Ser. No. 14/989,182, filed Jan. 6, 2016, which is a continuation-in-part application of U.S. application Ser. No. 12/824,509, filed Jun. 28, 2010, now abandoned, which claims benefit of priority to U.S. Provisional Application Ser. No. 61/222,141, filed Jul. 1, 2009, the contents of which are incorporated herein by reference in their entireties.

BACKGROUND OF THE INVENTION

The necessary condition for the reduction of body mass is a negative energy balance. Energy intake must be consistently lower than energy expenditure in order for weight loss to occur. Therefore, any weight control strategy must address one or both parts of the energy equation; intake or expenditure. With regard to the control of energy intake, two broad strategies can be adopted: the enhancement of the satiety response to food or the blockade of absorption. The physical and chemical properties of various foods can be used to achieve both effects.

With specific regard to the modulation of appetite, those processes responsible for the termination of a meal and the suppression of subsequent intake are of particular interest. The within meal processes of satiation and the post-meal end state of satiety are generated by the sensory, physical and chemical characteristics of the food consumed. The strength of these signals determines meal duration and meal size, and the length of the post-meal interval before the next eating occasion. The activation of such signals can be employed to enhance the appetite response to food and limit caloric intake.

Various naturally occurring ingredients including herbal extracts have been shown to produce beneficial effects on appetite and weight control when used as supplements or food components (Ruxton, et al. (2005) Br. Food J. 107: 111-125; Ruxton, et al. (2007) Br. Food J. 109: 416-428). ZOTRIM is a mixed herbal preparation containing Yerbe Maté, Guarana and Damiana, common ingredients of commercially available drinks, and the product is available in the UK as a food supplement. This herb extract formulation significantly delays gastric emptying, reduced the time to perceived gastric fullness and induced significant weight loss over 45 days in overweight patients (Anderson & Fogh (2001) J. Hum. Nutr. Dietet. 14:243-250). A consumer study has also been undertaken to test the efficacy of this preparation in the field. A total of 48 free-living subjects completed a 28-day trial and demonstrated a self-reported mean weight loss of 2.3 kg. Questionnaire data suggested that subjects ate less at meals and snacked less frequently (Ruxton (2004) Nutr. Food Sci. 34:25-28; Ruxton, et al. (2005) Nut. Food Sci. 35:303-331; Ruxton, et al. (2007) supra). However, the effects of ZOTRIM on human food intake, feeding behaviour and subjective feelings of appetite and satiety were not determined.

FIBRESURE is a 100% natural fiber supplement that can be taken daily. The term fiber covers a wide variety of substances belonging to the family of carbohydrates that resist hydrolysis by human alimentary enzymes but are fermented by colonic micro flora (Bianchi & Capurso (2002) Dig. Liver Dis. 34(Suppl 2):S129-33). Fiber is normally connected with increases in satiety due to its high viscosity and bulking effect (Burton-Freeman (2000) J. Nutr. 130: 272S-275S). However, FIBRESURE is a fiber product with little effect on viscosity. Current recommendations for the management of obesity and diabetes mellitus include an increase in dietary fiber intake, as it may contribute to lower fasting and postprandial plasma glucose concentrations and improvement of glycaemic control, which can help control energy intake (Vinik & Jenkins (1988) Diabetes Care 11:160-173). FIBRESURE contains the soluble fiber inulin, which is a prebiotic carbohydrate derived from chicory root. Inulin and inulin-type fructans are mostly oligosaccharides or oligofructoses and stimulate colonic production of Short Chain Fatty Acids (SCFAs), (Guarner (2005) Brit. J. Nutr. 93:S61-5). Fiber fermentability which produces SCFA has been linked with increasing satiety (Bosch (2008) Br. J. Nutr. 102:318-325).

The mechanism by which inulin and inulin-type fructans exert a satiating effect has not been identified. There are many gastrointestinal peptides that affect food intake such as ghrelin, cholecystokinin (CCK), glucagon-like peptide-1 (7-36) amide (GLP-1), oxyntomodulin, peptide YY (PYY) and pancreatic polypeptide (PP). Fructans modulate gastrointestinal peptides involved in the control of food intake, particularly GLP-1 and ghrelin (Orskov, et al. (1989) J. Biol. Chem. 264(22):12826-12829). GLP-1 is an anorectic peptide secreted by the L-cells which suppresses meal-induced gastric acid and pancreatic juice secretion and slows gastric emptying (Schjoldager, et al. (1989) Dig. Dis. Sci. 34:703-708). There are several studies showing that peripheral injection of GLP-1 decreases food intake and consequently body weight in rats and human subjects, (Meier, et al. (2002) Eur. J. Pharmacol. 440:269-279; Zander, et al. (2002) Lancet 359:824-830). Ghrelin is associated with the mesolimbic cholinergic dopaminergic reward system. This reward link is composed of cholinergic input from the laterodorsal tegmental area to the mesolimbic dopamine system that originates in the ventral tegmental area and projects to the nucleus accumbens (Jerlhag, et al. (2007) Addict. Biol. 12(1):6-16). In this respect, treatment of human volunteers with approximately 20 g of oligofructose per day for 7 days increased serum GLP-1 levels (Piche, et al. (2003) Gastroenterology 124(4):894-902). Furthermore, in a study of 14 healthy volunteers, it was found that the gut peptide GLP-1 decreases motility in the antro-duodeno-jejunal region thus inducing satiety (Hellstrom, et al. (2008) Neurogastroenterol. Motil. 20(6):649-59).

SUMMARY OF THE INVENTION

This invention is composition for suppressing appetite about 150 to 450 mg of yerba maté leaf extract, about 150 to 360 mg of guarana seed extract, about 60 to 150 mg of damiana leaf extract, and about 2 to 10 grams of isolated, fermentable inulin. In certain embodiments, the composition is formulated as a sachet, solid food product, dairy product, breakfast cereal, muesli, candy, confectionary, cookie, biscuit, cracker, chocolate, chew, chewing gum, dessert, powdered drink or liquid comestible.

DETAILED DESCRIPTION OF THE INVENTION

It has now been found that a combination of selected herbal extracts (i.e., yerbe maté extract, guarana extract, damiana extract) and dietary fiber can significantly decrease food intake compared to use of the herbal extracts alone or dietary fiber alone. Specifically, the combination of herbal extract and dietary fiber described herein provided a significant reduction in gram (91.4 g, 24.3%) and kcal intake (202. kcal, 26.7%) as compared to placebo-water. Further, the combined administration of herbal extract and dietary fiber produced a significant reduction in gram intake compared to placebo in all food groups except low fat sweet items; intake of high fat savory items was reduced by 18.5 g (27.6%), low fat savory intake reduced by 19.1 g (13.6%) and the greatest reductions were seen for high fat sweet items where intake was reduced by 31.1 g (48.8%). The study herein demonstrated a signficant and robust effect on food intake of a standard ad libitum lunch. Accordingly, the present invention features a composition composed of yerbe maté extract, guarana extract, damiana extract and a dietary fiber for use in reducing food consumption and/or calorie intake.

As is conventional in the art, appetite is a natural desire, or longing for food. According to the present invention, increased appetite generally leads to increased feeding behaviour. In this respect, an appetite suppressant is a composition that decreases the desire for food, as evidenced by a decrease in food consumption and/or calorie intake.

The composition of the present invention is composed of soluble extracts of yerbe maté (leaves of *Ilex paraguayensis, I. vomitora*, or *I. dahoon*), guarana (seeds of *Paullinia cupana* or *P. sorbalis*) and damiana (leaves of *Turnera diffusa* var. *aphrodisiaca, T. opifera*, or *T. ulmifoliei*). Soluble extracts of the invention can be prepared by conventional methods of drying and/or grinding plant biomass and subjecting the same to one or more suitable solvents, thereby providing an extract, which may be either used as a crude extract or further fractionated.

Suitable methods for drying plant biomass include: sun drying followed by a heated air-drying or freeze-drying; lyophilization or chopping the biomass into small pieces, e.g., 2-10 cm, followed by heated air-drying or freeze-drying. Once sufficient moisture has been removed, e.g., more than 90%, the material can be ground to a coarse particle size, e.g., 0.01-1 mm, using a commercial grinder. For laboratory scale extraction, a coffee grinder or equivalent can be used.

In general terms, a suitable method for preparing an extract of plant biomass includes the steps of treating collected plant biomass with a solvent to extract a fraction having appetite suppressant or curbing activity, separating the extraction solution from the rest of the plant biomass, removing the solvent from the extraction solution and recovering the extract. The extract so recovered may be further purified by way of suitable extraction or purification procedures.

More specifically, plant biomass can be ground to a coarse powder as described above. Subsequently, a suitable solvent, e.g., a food grade solvent, can be added to the powder. A good grade solvent is any solvent which is suitable and approved for use in conjunction with foods intended for human consumption. Examples of suitable solvents are alcohol-based solvents, ethyl acetate, liquid carbon dioxide, hexane, and one or more components of fusel oil, e.g., ethyl acetate. Alcohol-based solvents, i.e., pure alcohol solvents and mixtures thereof with water or other organic solvents, are most desirable.

The extraction solution can then be separated from the residual plant biomass by an appropriate separation procedure such as filtration and/or centrifugation. The solvent can be removed, e.g., by means of a rotary evaporator. The separated crude extract can then be tested to confirm appetite suppressant or appetite curbing activity in a suitable in vivo bioassay.

A suitable and accepted in vivo model for measuring appetite suppression or appetite curbing activity in an animal model is described in Example 2. A clinically effective and medically approved anti-obesity drug, e.g., sibutramine, can be used as a positive control for reduction in food intake in this model. Positive results from this test model are an indicator of clinical efficacy in the human context. Alternatively, suppression, reduction or curbing of appetite can be assessed by any of the methods referred to in WO 98/46243.

Plant extracts of the invention can be dried to remove moisture, e.g., by spray-drying, freeze-drying or vacuum-drying, to yield a free-flowing powder. Optionally, the extracts can be dried on a pharmaceutically acceptable carrier, such as maltodextrin or starch. As yet a further alternative, plant biomass can be extracted and concentrated without drying to give a liquid extract, which is effective in curbing or suppressing appetite.

In addition to yerbe maté, guarana and damiana extract, the composition of the invention can further include one or more of: extracts from the leaves of Buchu (*Barosma betulina, B. crenulata, B. serratifolia*) containing diosphenol (buchu camphor); extracts from the leaves or flowers of Vervain (*Verbena officinales, V. jamaicensis, V. lappulacae, V. hesitate, V. urticifolia, V. Sinuata*) containing glycosides, adenosine, essential oils, tannin, livertin and/or emulin; extracts of Kola nut (*Cola nitida, C. vera*) containing caffeine; or extracts from the leaves or flowers of Ginseng (*Panax ginseng, P. quinquefolius* L.) containing triterpenoid saponins.

In addition to herbal extracts, the present composition also features a dietary fiber. As used herein, dietary fiber is the indigestible portion of plant foods that pushes food through the digestive system and absorbs water. Dietary fiber can be soluble (able to dissolve in water) or insoluble (not able to dissolve in water). Soluble fiber, like all fiber, cannot be digested. But it does change as it passes through the digestive tract, being transformed or fermented by bacteria therein. In contrast, insoluble fiber passes through the body largely unchanged. Accordingly, in particular embodiments of the present invention, the dietary fiber is fermentable or soluble.

Fermentable dietary fiber can be obtained from a variety of plant foods, including, but not limited to legumes (e.g., peas, soybeans, and other beans); grains such as oats, rye, chia, and barley; some fruits and fruit juices including prune juice, plums, berries, bananas, and the insides of apples and pears; certain vegetables such as broccoli, carrots and Jerusalem artichokes; root vegetables such as potatoes, sweet potatoes, and onions; and psyllium seed husk. In particular embodiments, the dietary fiber is isolated and/or substantially purified to homogeneity, e.g., at least to 75%, 80%, 85%, or 90%, homogeneity or up to 99% homogeneity.

For use in accordance with the present invention, the isolated, fermentable dietary fiber is inulin, a beta-glucan, a pectin, a natural gum, an oligosaccharide, psyllium seed husk, a resistant dextrin, an alginate or a combination thereof. Inulin, belonging to the class of fibers known as fructans, is typically extracted from enriched plant sources such as chicory roots or Jerusalem artichokes. Beta-glucans, polysaccharides of D-glucose monomers linked by glycosidic bonds, are typically isolated from oat bran, whole oats, oatrim or rolled oats. Pectins, a complex set of polysaccharides that are present in most primary cell walls and particularly abundant in the non-woody parts of terrestrial plants, are composed of a linear chain of α-(1-4)-linked D-galacturonic acid that forms the pectin-backbone. Natural gums, which are polysaccharides of natural origin that are capable of causing a large viscosity increase in solution, include, but are not limited to xanthan gum, acacia gum or guar gum. Alginate is a soluble fiber extracted from seaweed. According to the present invention, oligosaccharides, saccharide polymers containing a small number (typically three to ten) of component sugars (also known as simple sugars), particularly include fructooligosaccharides. As is conventional in the art, a resistant dextrin is a water-soluble dietary fiber obtained by, e.g., subjecting starch to high-temperature heating and enzymatic hydrolysis with α-amylase and glucoamylase. The selection of the dietary fiber to be used in the composition of the present invention can be dependent upon the form of the composition and the manner in which the formulation is administered, e.g., as multiple different formulations or as one formulation containing yerbe maté extract, guarana extract, damiana extract and dietary fiber. In particular embodiments, the dietary fiber of the instant composition is inulin.

According to this invention, the herbal extracts and dietary fiber can be provided as a composition prepared as individual formulations (e.g., the composition includes or comprises a formulation containing yerbe maté extract, a formulation containing guarana extract, a formulation containing damiana extract, and a formulation containing a dietary fiber), or the composition can be prepared as a combination of formulations (e.g., the composition includes or comprises a formulation containing yerbe maté extract, guarana extract, and damiana extract; and a formulation containing a dietary fiber), or the composition can be prepared as a single unitary formulation (e.g., the composition includes or comprises a formulation containing yerbe maté extract, guarana extract, damiana extract, and dietary fiber). Moreover, when the composition is prepared as individual or a combination of formulations, said formulations can be the same, e.g., all tablets; or different, e.g., a capsule formulation and a liquid formulation. In addition, when taken as individual formulations, said formulations can be taken simultaneously or consecutively, e.g., within minutes of each other.

Soluble plant extracts, dietary fiber or a combination thereof can be admixed by conventional compounding procedures with any conventional pharmaceutical or nutritionally acceptable excipient, diluent or carrier in the preparation of pharmaceuticals, nutraceuticals, nutritional compositions, such as dietary supplements, slimming compositions, medical nutrition or functional foods. Typically, this involves mixing the active ingredients of the invention together with edible pharmaceutically or nutritionally acceptable solid or liquid carriers and/or excipients, e.g., fillers, such as cellulose, lactose, sucrose, mannitol, sorbitol, and calcium phosphates; and binders, such as starch, gelatin, tragacanth, methylcellulose and/or polyvinylpyrrolidone (PVP). Optional additives include lubricants and flow conditioners, e.g., silicic acid, silicon dioxide, talc, stearic acid, magnesium/calcium stearates and polyethylene glycol (PEG) diluents; disintegrating agents, e.g., starch, carboxymethyl starch, cross-linked PVP, agar, alginic acid and alginates, coloring agents, flavoring agents and melting agents. Dyes or pigments may be added to tablets or dragee coatings, for example, for identification purposes or to indicate different doses of active ingredient.

The composition of the invention can optionally include conventional food additives, such as any of emulsifiers, stabilizers, sweeteners, flavorings, coloring agents, preservatives, chelating agents, osmotic agents, buffers or agents for pH adjustment, acidulants, thickeners, texturizers and the like.

Suitable product formulations according to the present invention include sachets, soft gel, powders, syrups, pills, capsules, tablets, liquid drops, sublinguals, patches, suppositories, and liquids. Also contemplated are food and beverage products containing the composition of the present invention, such as solid food products, like bars (e.g., nutritional bars or cereal bars), powdered drinks, dairy products, breakfast cereals, muesli, candies, confectioneries, cookies, biscuits, crackers, chocolate, chews, chewing-gum, desserts and the like; liquid comestibles, like soft drinks, juice, sports drinks, milk drinks, milk-shakes, yogurt drinks or soups, as well as pet treats, pet foods, etc.

The composition of the invention can be provided as a component of a normal meal, e.g., a nutritional or slimming composition, or dietary supplement, in the form of a health drink, a snack or a nutritionally fortified beverage, as well as a pill, a tablet or a softgel, for example. When used as a snack or dietary supplement it will preferably be consumed between or before meals.

Optionally, the composition according to the invention can be nutritionally complete, i.e., may include vitamins, minerals, trace elements as well as nitrogen, carbohydrate and fatty acid sources so that it may be used as the sole source of nutrition supplying essentially all the required daily amounts of vitamins, minerals, carbohydrates, fatty acids, proteins and the like. Accordingly, the composition of the invention may be provided in the form of a nutritionally balanced complete meal, e.g., suited for oral or tube feeding.

In addition to the herbal extracts and dietary fiber, the composition of the invention may also include one or more further active ingredients, e.g., capsaicin (red pepper); fatty acids, especially linoleic acid (LA) and conjugated linoleic acid (CLA); glycomacropeptide (GMP); Long Chain Triglyceride (LCT); enterostatin; galactose; glucuronic acid; hydroxycitrate (HCA); citrus; β-hydroxy butyrate; medium chain tryglycerides (MCTs); D-tagatose; caffeine; potato extract; green tea extract; epigallocatechin gallate, or other catechins; peptide D4; vitamins B (e.g., Vitamin B3 and/or B6), C and/or E; and chromium picolinate. By way of illustration, the composition can include about 6.9 mg Vitamin B3, 0.84 mg Vitamin B6 and/or 20 mg Vitamin C. Alternatively, the composition of the invention may be combined with an anti-obesity drug, such as sibutramine. For example, the composition of the invention may be provided in the form of a kit for separate, sequential or simultaneous administration in conjunction with an anti-obesity drug such as orlistat (XENICAL™), Hoodia extract, and the like.

Daily dosage of a composition of the present invention would usually be single or multiple servings per day, e.g., once or twice daily, for acute or chronic use. However, benefit may be derived from dosing regimens that can include consumption on a daily, weekly or monthly basis or any combination thereof. Administration of compositions of the invention, e.g., treatment, could continue over a period of days, weeks, months or years, in order, for example, to constantly control the weight, or until a healthy or cosmetically beneficial loss of body weight has occurred. Optimally, the composition of the invention is consumed at least once a day on a regular basis, prior to (i.e., pre-prandial administration), or during a meal. Preferably, the composition of the invention is consumed prior to a meal.

The amount and dosage regimen of the composition of the invention to be administered is determined in the light of various relevant factors including the purpose of administration, the age, sex and body weight of an individual subject, i.e., inter alia on the severity of the subject's obesity or overweight. In this respect, the compositions of the invention can be administered under the supervision of a medical specialist, or may be self-administered.

Preferred delivery formats for the appetite suppressing or appetite curbing composition of the invention, would be as a sachet, solid food product, dairy product, breakfast cereal, muesli, candy, confectionary, cookie, biscuit, cracker, chocolate, chew, chewing gum, dessert, powdered drink or liquid comestible containing about 150 mg to about 450 mg, or preferably about 300 mg to about 360 mg, dry weight of yerbe maté extract; about 150 mg to about 360 mg, or preferably about 270 mg to 300 mg, of gaurana extract; about 60 mg to about 150 mg, or preferably about 90 mg to about 120 mg, of damiana extract; and about 2 grams to about 10 grams, or preferably about 5 grams to 7 grams, of dietary fiber, in particular inulin.

An illustrative example of a formulation of herbal extracts is 27.5% weight yerbe maté extract, 23.2% weight Guarana, 9% weight Damiana extract, and 40.3% weight of dicalcium phosphate, talc, sodium carboxymethylcellulose, magnesium stearate and hydroxypropylmethylcellulose as additional ingredients.

The present invention also features a method for decrease food intake and/or suppressing appetite by administering to a subject in need thereof an effective amount of yerbe maté extract, guarana extract, and damiana extract in combination with a dietary fiber. Administration of the composition of the present invention results in a 10% to 40% decrease in food consumption (gram weight) or a 10% to 35% decrease in calorie intake (Kcal) as compared to a subject not receiving the composition. In particular embodiments, the composition of the present invention achieves a 20 to 30% reduction in food consumption or calorie intake, levels which unexpectedly surpass other nutritional weight loss compositions. For example, while humans studies analyzing the effects of *Caralluma fimbriata* have shown a 8.2% reduction in energy intake (Kuriyan, et al. (2007) *Appetite* 48:338-344), human studies of sodium alginate showed a 7% reduction in energy intake (Paxman, et al. (2008) Appetite 51:713-719), human studies of oligofructose (soluble fermentable non-viscous fiber) have shown a 5% reduction in total intake (Cani, et al. (2006) *Euro. J. Clin. Nutr.* 60:567-572), and human studies of hydroxycitric acid (HCA-SX) and a combination of HCA-SX and niacin-bound chromium (NBC) and *Gymnema sylvestre* extract (GSE) have shown a 4% decrease in food intake (Preuss, et al. (2004) *Nutr. Res.* 24:45-58), human studies with a natural dietary compound of chromium picolinate, inulin, capsicum, L-phenylalanine, and other lipotropic nutrients has not shown any significant difference in energy intake (Hoeger, et al. (1998) *Adv. Ther.* 15:305-14). Similarly, food intake and appetite ratings were not significantly reduced when either beta-glucan and fructooligosaccharides are used alone or in combination (Peters, et al. (2009) *Am. J. Clin. Nutr.* 89:58-63; Kim, et al. (2006) *Cer. Foods World*, pg. 29), or with a fiber system of alginate and guar gum (Mattes (2007) *Physiol. Behav.* 90:705-711), or with supplements of fermentable fibers (pectin, beta-glucan) and non-fermentable methylcellulose (Howarth, et al. (2003) *J. Nutr.* 133:3141-3144). Indeed, the levels of reduction in food/calorie intake of the instant composition are more comparable to pharmacological options including sibutramine (12-26% reduction; Rolls, et al. (1998) *Obes. Res.* 6:1-11; Chapelot, et al. (2000) *Physiol. Behav.* 68:299-308), diethylpropion (11-15% reduction; Porikos, et al. (1980) *Clin. Pharmacol. Ther.* 27:815-822), fluoxetin (13-16% reduction; McGuirk & Silverstone (1990) *Int. J. Obes.* 14:361-72) and fenfluramine/d-fenfluramine (17-22% reduction; Goodall & Silverstone (1988) *Appetite* 11:215-288. See, also, Halford, et al. (2007) Drugs 67:27-55 and Halford, et al. (2004) *Curr. Drug Targets* 5:221-40.

Subjects benefiting from the method of the invention include those in need of weight loss, e.g. overweight or obese subjects, as well as subjects controlling food intake so as not to gain weight. In some embodiments, subjects receiving the composition of this invention are average or slightly overweight, i.e., having a BMI of 18.5-29.9 kg/m$^2$. In other embodiments, subjects receiving the composition of this invention are overweight, i.e., having a BMI of greater than 29.9 kg/m$^2$. In further embodiments, subjects benefiting from the method of the invention are those that consume high fat food, e.g., food containing greater than 8 g of fat per 100 g.

In addition to the uses described therein, the invention further provides a composition according to the invention for use in suppressing appetite.

The invention additionally provides the use of yerba mate extract, guarana extract, daminiana extract and a dietary fiber in the manufacture of a composition for suppressing appetite.

The invention is described in greater detail by the following non-limiting examples.

Example 1: Materials and Methods

Study Design. This was a double-blind, placebo-controlled study using a randomized within-subject design to evaluate the effects of ZOTRIM and inulin fiber given together, separately and against placebo control in terms of food intake in grams and kilocalories and subsequent food ratings measured using visual analogue scales (VAS) of hunger, fullness, prospective consumption, desire to eat and satisfaction pre dosing, pre and post meals and at hourly intervals across the day. The independent variables were the four conditions-ZOTRIM (tablet form) and inulin fiber (powder mixed with water), ZOTRIM and control, inulin fiber and placebo and control and placebo. The dependant variables were food intake measured in grams, kilocalories and macronutrients and the VAS ratings. All food and water was recorded by weight scales (Sartorius Model CPA 4202S, Sartorius Ltd, Epsom, UK; 0.1 gram accuracy) before and after meals to ascertain intake in grams, kilocalories and macronutrients, and food choice. There were two VAS's: the first was given nine times throughout the study day and measured hunger, fullness, prospective consumption, desire to eat, satisfaction, nausea and thirst. The second VAS measured pleasantness, palatability, tastiness, saltiness and sweetness and was given after breakfast and lunch. The product/placebo was administered 15 minutes before breakfast and lunch which were four hours apart. Participants were randomized to the study by means of a block plan created on an internet-based randomization program.

Participants. Fifty-eight healthy, average and slightly overweight (body mass index [BMI]: 18.5-29.9 kg/m$^2$) women completed the study. Volunteers were recruited by advertisement. Upon response to the advertisements, individuals completed a standardized telephone or email interview to assess their age, height, weight, occupation, smoking status and ability to attend the study center at the requisite times. Those who were aged over 65, with a BMI<18.5 kg/m$^2$ or >29.9 kg/m$^2$, who disliked more than 25% of the ad-libitum lunch study foods, were smokers, currently dieting, or who did not eat regular meals, were not studied further.

Initial Screening. Following the initial telephone/email interview, potential participants received detailed information on the protocol, and were invited to the study center, (The Kissileff Laboratory for the Study of Ingestive Behaviour in the School of Psychology, The University of Liverpool), for a full screening no more than 21 days before commencing the study. All volunteers signed an informed consent before any study-specific procedures were undertaken. Confidentiality and anonymity were assured.

At screening, the following measurements were taken: height measured without shoes, using a stadiometer to the nearest cm and weight using standard calibrated scales to the nearest 0.1 kg. Participants also completed a medical history, diet history, and eating behaviour questionnaire (The Dutch Eating Behaviour Questionnaire [DEBQ-R]).

Exclusion Criteria. Following screening, participants were excluded from the study if they reported any of the following: significant health problems; not having dieted in the last 12 months to lose or control weight; currently adhering to a specific food avoidance diet; gastrointestinal symptoms requiring treatment; bariatric surgery; systemic or local treatment likely to interfere with evaluation of the study parameters; taking medication known to affect appetite or weight within the past month and/or during the study; pregnant or planning to become pregnant or breastfeeding; history of anaphylaxis to food; general or specific food allergies, including caffeine and any of the study foods; dislike of more than 25% of the ad-libitum study foods; extreme dietary restraint; non breakfast eaters; working in nutrition, dietetics, food research, food manufacturing or supplements industry.

Those participants who fulfilled the study criteria were recruited to the study and assigned a code number.

Study Supplement. The ZOTRIM formulation contained 112 mg Yerbe Mate, 95 mg Guarana and 36 mg Damiana. Guarana, a dough made from the seeds of *Paullinia cupana*, which grows in Brazil and Venezuela, contains 3-6% caffeine, 5-8.5% tannins, 7.8% resins, 2-3% lipid, 0.06% saponin, 5-6% starch and 1.5% coloring agents (Schery (1954) *Plants for Man*. London: George Allen and Unwin, pp. 518-519). Yerbe Maté is an extract of *Ilex paraguayensis* from Brazil, Argentina and Paraguay containing 1-1.5% caffeine, 4-10% tannins and 3% resins and lipids (Hill (1952) *Economic Botany*. New York: McGraw-Hill Book Company, pp. 479-481.). Damiana is obtained from the leaves of the plant Turnera *diffusa* var. *aphrodisiaca* from California, Mexico, Brazil and Bolivia and contains ethereal oils, resins and tannins (Bradley (1992) *British Medical Compendium*, Vol. 1. London: British Herbal Medical Association, pp. 71-72.).

The placebo contained lactose and other ingredients minus the active ingredients. ZOTRIM and placebo were supplied as individual tablets and packaged in coded containers labeled A or B to ensure the double-blind status of the study. All capsule components (active and inert ingredients) were those approved and commonly used for commercial supplements and health ingredients and produced by a commercial capsule manufacturer. The inulin fiber (FIBRESURE) was derived from chicory root and packaged in powder form in 5.8 g individual stick packs, containing 5 g fiber per pack. Each dose of 5 grams of fiber was mixed into 100 grams of water.

Participants were instructed to take the dose of 3 tablets with a glass of water (100 g) 15 minutes before their two main meals of each day. The order of treatments was counter-balanced across the four treatment conditions, with inulin being mixed in or not mixed into the water according to condition.

Materials and Tools. VAS were used to rate degree of hunger, fullness, satisfaction, desire to eat, perception of how much participants could eat (prospective consumption), thirst and nausea. VAS was composed of 100 mm horizontal lines anchored by "not at all" and "extremely" at opposite ends, upon which participants record with a vertical line their subjective ratings. For example, hunger was rated along a 100 mm line that was preceded by the question "how hungry do you feel at this moment?" and anchored on the left by "not at all hungry" and on the right by "extremely hungry", or "how pleasant was the breakfast?" being anchored on the left by "not at all pleasant" and on the right by "extremely pleasant".

Participants completed these ratings nine times (T1-T9) during each test day. The exact times were: pre dose pre breakfast (T1), pre breakfast (T2), post breakfast (T3), Interval 1 (T4), Interval 2 (T5), Interval 3 (T6), pre dose pre lunch (T), pre lunch (T8), and post lunch (T9) Pleasantness VAS were completed at two time points, viz; post breakfast and post lunch.

Procedure. At the screening visit, participants were asked if they had read and understood the information sheet concerning the study (which they were sent a minimum of two days before the screening visit). Participants were then asked to sign two copies of the consent form. Participants' height and weight were measured. BMIs were calculated ensuring they were in a suitable range for the study. Participant's medical history and weight control history were taken. A DEBQ and list of study foods were shown to the participants to ensure that they did not have any objections or intolerances to the study foods. Following the screening, participants were contacted to determine whether or not they were able to continue in the study. Successful participants then received an information pack which contained details of their agreed times to visit the lab. Participants were asked to fill in an evening food and activity diary prior to attending the visits.

Visit two took place at a minimum of two days after screening. Subsequent visits took place as soon as possible leaving two days between visits (giving a total of four visits). Breakfast was served between 8:30 AM and 9:45 AM (time depending on when researcher and participant had arranged to meet at lab). If participants failed to attend their visit within these time limits, their session was rescheduled for another day.

The protocol for the laboratory visits (four in total) was as follows: On the day preceding each study day participants were asked to keep their food intake, fluid intake and activity levels similar and not to consume any alcohol. On each pre-study evening participants were requested to record in a diary the food and drink they consumed and the activities they undertook from 5:00 PM until they retired for the night. They were asked not to eat or drink anything except water from 12:00 midnight until they attended at the study center the following morning.

At 8:30 AM on each study day participants attended the study center. The diary was collected and participants were given instructions on completing the VAS, before filling in the first set of VAS ratings (T1). The pre-breakfast dose of product/placebo and a glass containing 100 ml water were presented to the participant 15 minutes before breakfast. They were instructed to consume all of the tablets with all of the water. They were weighed and details of compliance were recorded. Participants were then seated in the testing area in individual cubicles. After completing the pre-breakfast VAS ratings (T2), participants were given a fixed-load breakfast as shown in Table 1, and were asked to consume everything presented within 20 minutes. After breakfast, participants completed a post-breakfast set of VAS appetite (T3) and pleasantness ratings, and were then free to leave the study center. They were instructed not to eat or drink anything except water that was provided by the study. They were asked to complete VAS ratings at hourly intervals (T4, T5 and T6) and to return to the study center three three hours and forty minutes after their first dose was given to ensure their second dose would be given on time. On their return, the VAS measures and remaining water (if any) were collected for assessment and a pre-dose VAS (T7) was completed. Fifteen minutes before lunch was to be served (four hours after breakfast had been served) the study product/placebo was presented with a glass containing 100 ml water and participants were instructed to swallow all of the tablets with all of the water.

TABLE 1

| Food* | Amount (g) | % | |
|---|---|---|---|
| Kellogg's Cornflakes | 30 | | |
| Semi-skimmed UHT Milk | 125 | | |
| Orange Juice | 200 | | |
| Sliced White Bread (toasted) | 60 | % Energy from Protein | 10 |
| Flora Margarine | 10 | % Energy from Fat | 17 |
| Strawberry Jam | 20 | % Energy from Carbohydrate | 73 |
| TOTAL WEIGHT | 445 | TOTAL KCALS | 496 |

*Also included hot drink, 35 g milk and sugar if required.

A 15-minute rest period followed, during which the participants remained in the study center. They then completed another VAS (T8) and were served an ad-libitum lunch as detailed in Table 2. Participants were instructed to eat as much as they liked from the choice of foods and water offered, taking as long as they wished, and signaling when they had finished. Immediately following ad-libitum consumption of the test meal, participants completed a set of post-lunch VAS ratings (T9).

Participants were then free to leave the study center. All food and water was weighed (Sartorius Ltd) to the nearest 0.1 g before and after each meal to determine intake. The length of each meal was timed by the study staff although participants were only instructed there was a time limit (of 20 minutes) at breakfast. After completion of the study participants were debriefed and were reimbursed for their time and travel expenses (if any).

Test Meals. A standard fixed-load breakfast (496 kcal) was dispensed to participants in all conditions (Table 1). In addition to the fixed-load breakfast, at the first visit, participants were offered a hot drink of tea or coffee with additional milk (35 g) and sugar if desired. If requested, this drink had to be consumed on each subsequent visit. The amount and energy composition of the ad-libitum cold test lunch items is listed in Table 2. The protein, carbohydrate and fat content of each test lung item are respectively listed in Tables 3-5. This meal was designed to offer a selection of high and low fat savory and sweet food items. Water (500 ml) was offered at the test meal. Participants were instructed to eat as much as they wished and to signal via a booth-based buzzer when they had finished.

TABLE 2

| Food | Amount (g) | Kcal/100 g | Kcal in Serving |
|---|---|---|---|
| Tesco Medium Sliced White Bread | 144.00 | 240.00 | 345.60 |
| Flora | 40.00 | 531.00 | 212.40 |
| Tesco Sandwich Turkey | 62.50 | 110.00 | 68.75 |
| Tesco Danish Salami | 44.60 | 495.00 | 220.77 |
| Tesco Medium Grated Cheddar | 100.00 | 415.00 | 415.00 |
| Cucumber | 80.00 | 10.00 | 8.00 |
| Walkers Ready Salted Crisps | 25.00 | 530.00 | 132.50 |
| Quaker Snack-a-jacks S&V | 30.00 | 410.00 | 123.00 |
| Tesco Value Cookies | 100.00 | 515.00 | 515.00 |
| Tesco Chocolate Mousse | 62.50 | 200.00 | 125.00 |
| Tesco Value Fruit Cocktail | 410.00 | 46.00 | 188.60 |
| Tesco Jelly Babies | 120.00 | 368.00 | 441.60 |
| Total | | | 2796.22 |

TABLE 3

| Food | Protein/100 g | Protein in Serving |
|---|---|---|
| Tesco Medium Sliced White Bread | 8.20 | 11.81 |
| Flora | 0.00 | 0.00 |
| Tesco Sandwich Turkey | 21.20 | 13.25 |
| Tesco Danish Salami | 13.20 | 5.89 |
| Tesco Medium Grated Cheddar | 24.40 | 24.40 |
| Cucumber | 0.70 | 0.56 |
| Walkers Ready Salted Crisps | 6.50 | 1.63 |
| Quaker Snack-a-jacks S&V | 6.50 | 1.95 |
| Tesco Value Cookies | 4.80 | 4.80 |
| Tesco Chocolate Mousse | 3.50 | 2.19 |
| Tesco Value Fruit Cocktail | 0.40 | 1.64 |
| Tesco Jelly Babies | 2.30 | 2.76 |
| Total | | 70.87 |

TABLE 4

| Food | Carbohydrate/100 g | Carbohydrate in Serving |
|---|---|---|
| Tesco Medium Sliced White Bread | 47.80 | 68.83 |
| Flora | 0.00 | 0.00 |
| Tesco Sandwich Turkey | 0.80 | 0.50 |
| Tesco Danish Salami | 7.00 | 3.12 |
| Tesco Medium Grated Cheddar | 1.40 | 1.40 |
| Cucumber | 1.50 | 1.20 |
| Walkers Ready Salted Crisps | 49.00 | 12.25 |
| Quaker Snack-a-jacks S&V | 77.00 | 23.10 |
| Tesco Value Cookies | 65.00 | 65.00 |
| Tesco Chocolate Mousse | 26.80 | 16.75 |
| Tesco Value Fruit Cocktail | 11.00 | 45.10 |
| Tesco Jelly Babies | 89.80 | 107.76 |
| Total | | 345.01 |

TABLE 5

| Food | Fat/100 g | Fat in Serving |
|---|---|---|
| Tesco Medium Sliced White Bread | 1.50 | 2.16 |
| Flora | 59.00 | 23.60 |
| Tesco Sandwich Turkey | 2.30 | 1.44 |
| Tesco Danish Salami | 46.00 | 20.52 |
| Tesco Medium Grated Cheddar | 34.40 | 34.40 |
| Cucumber | 0.10 | 0.08 |
| Walkers Ready Salted Crisps | 34.00 | 8.50 |
| Quaker Snack-a-jacks S&V | 8.00 | 2.40 |

TABLE 5-continued

| Food | Fat/100 g | Fat in Serving |
|---|---|---|
| Tesco Value Cookies | 26.10 | 26.10 |
| Tesco Chocolate Mousse | 8.40 | 5.25 |
| Tesco Value Fruit Cocktail | 0.00 | 0.00 |
| Tesco Jelly Babies | 0.00 | 0.00 |
| Total | | 124.44 |

Lunch time was fixed at precisely 4 hours after breakfast. All meals were served in individual booths in the test study center.

Adverse Events. If participants reported any adverse events they had experienced while taking the study supplement the type, severity, date of onset and resolution were recorded.

Statistical Analysis. Analysis was performed using SPSS for WINDOWS, Version 16 (SPSS Inc., Chicago, US). Analysis of variance (ANOVA) and post-hoc paired t-tests were used. The assumptions of the ANOVA model were tested and if homogeneity of variance was not found, multivariate tests were adopted for that variable. All tests were two-tailed unless stated. Bonferroni corrections were applied for multiple comparisons.

Intake at the test meal was initially analyzed for amount consumed (in grams and kcal) using a two-way ANOVA with condition (inulin fiber and ZOTRIM) as within-subject factors. Because breakfast was fixed, this was not included in the statistical analysis. Paired t-tests were used to investigate any significant differences. This analysis was then re-run incorporating the kcal content of breakfast and the kcal content in the inulin fiber conditions. A two-way ANOVA with inulin and ZOTRIM as within subject factors was performed to analyze food choice at the test meal. Kcal intake of high and low fat savory and high and low fat sweet items were compared between conditions.

Subjective parameters (e.g., hunger, gastric fullness) rated on the VAS were analyzed using a within-subjects repeated measures ANOVA with condition (ZOTRIM and placebo) and time (pre-dose pre-breakfast, pre-breakfast, post-breakfast, 10 AM, 11 AM, 12 PM, pre-dose pre-lunch, pre-lunch, post-lunch, 2 PM, 3 PM, 4 PM, and 5 PM; T1-T13) as within-subject factors. If a time-by-condition interaction effect was found significant, paired t-tests were conducted at each rating time between conditions.

Example 2: Herbal Extracts and Inulin Decrease Food Intake

Fifty-eight healthy average to slightly overweight women were recruited to the study through advertising. A double blind, placebo-controlled, cross-over design was employed. After screening, eligible participants were invited to the laboratory on four separate occasions for breakfast and lunch. The study days were arranged according to the participants' availability and always leaving a minimum of two days between each visit. On study days, the participants were administered the first dose of ZOTRIM and inulin fiber (5.8 g), ZOTRIM and water, inulin fiber and placebo or water and placebo, 15 minutes before a fixed load breakfast. Four hours after the initial dose, and 15 minutes before lunch, the second dose of the same condition was given. The dose was composed of three tablets, either ZOTRIM (a dose having 336 mg of yerba mate leaf extract, 285 mg of guarana seed extract and 108 mg of damiana leaf extract) or a placebo, and a hundred grams of water into which inulin fiber was or was not mixed according to condition. Participants were then offered an ad-libitum buffet lunch and the intake of each item of lunch was measured. Appetite was assessed using VAS.

In total 71 participants were screened, 62 were recruited and 58 completed the study. Nine participants were excluded, six as their BMI was >29.9, two due to medication they were taking and one as her BMI was <18.5. Of the four that were recruited to the study but did not complete it, three could not fit the visits around previous commitments and one could not be contacted after her first visit. Their data has been excluded from analysis.

The demographic (age), and anthropometric (weight, height, BMI) characteristics of the completing participants are shown in Table 6.

TABLE 6

| | Mean (±SD, n = 58) |
|---|---|
| Age (years) | 21.31 ± 3.79 |
| Weight (kg) | 60.16 ± 6.09 |
| Height (m) | 166.24 ± 5.23 |
| Body Mass Index (BMI) [kg/m$^2$] | 21.78 ± 1.99 |
| DEBQ | 2.56 ± 1.92 |

Intake at Test Meal. Total mean number of grams (g) and kilocalories (kcal) consumed in each condition are displayed in Table 7.

TABLE 7

| | Number (N) | Mean Intake in Grams (g) (±SD) | Mean Intake in Kilocalories (kcal) (±SD) |
|---|---|---|---|
| Condition A (placebo) | 58 | 375.60 (±138.46) | 752.14 (±296.27) |
| Condition B (ZOTRIM) | 58 | 328.96 (±177.20) | 619.94 (±263.51) |
| Condition C (FIBRESURE) | 58 | 356.50 (±144.38) | 662.30 (±311.69) |
| Condition D (ZOTRIM and FIBRESURE) | 58 | 284.20 (±105.47) | 549.78 (±182.16) |

Gram Intake. A 2×2 repeated measures ANOVA demonstrated a significant main effect of ZOTRIM on gram intake ($F(1, 57)=26.110$, $p<0.001$). The ANOVA also demonstrated a significant main effect of inulin fiber on gram intake across conditions, ($F(1, 57)=12.661$, $p=0.001$). There was no interaction between ZOTRIM and fiber conditions ($F(1, 57)=1.841$, $p=0.180$) on gram intake.

Paired samples t-tests showed that there was a significant reduction in gram intake from control of 46.6 grams (12.4%) in the ZOTRIM condition ($t(57)=3.254$, $p=0.002$) and of 91.4 grams (24.3%) in the ZOTRIM and fiber condition combined ($t(57)=5.757$, $p<0.001$). The reduction in intake of 19.1 gram (5.1%) from control in the inulin only condition compared to the control condition proved insignificant ($p=0.188$). Intake was significantly lower in the ZOTRIM and fiber combined condition versus the ZOTRIM alone ($t(57)=3.852$, $p<0.001$) or fiber alone conditions ($t(57)=4.624$, $p<0.001$).

Energy Intake. A 2×2 repeated measures ANOVA demonstrated a significant main effect of ZOTRIM on caloric intake ($F(1, 57)=16.681$, $p<0.001$). The ANOVA also demonstrated a significant main effect of inulin fiber on caloric intake across conditions, (F(1, 57)=13.366, p=0.001). There was no interaction between ZOTRIM and fiber conditions (F(1, 57)=0.193, p=0.662).

Paired samples t-tests showed there was a significant reduction in caloric intake from control of 132.2 kcal (17.6%) in the ZOTRIM condition (t(57)=3.365, p=0.001), of 89.9 kcal (11.9%) in the fiber condition (t(57)=2.621, p=0.011) and of 202.4 kcal (26.9%) in the ZOTRIM and inulin fiber condition combined (t(57)=5.629, p<0.001). Caloric intake was significantly lower in the ZOTRIM and fiber combined condition versus the ZOTRIM alone (t(57)= 2.504, p=0.015) or fiber alone conditions (t(57)=3.178, p=0.002).

Analysis of the time taken to consume the ad-libitum lunch revealed a significant main effect of ZOTRIM (F (1,57)=4.196, p=0.045). There was no effect of inulin fiber (F (1,57)=0.010, p=0.921) and no interaction between ZOTRIM and inulin fiber (F (1,57)=3.316, p=0.074). Paired samples t-test showed there was a shorter lunch duration with ZOTRIM alone compared to placebo (t(57)=2.903, p=0.005).

Food Choice. The twelve food items offered at the ad-libitum lunch were analyzed according to variation in fat content and taste. Foods offered were grouped into high fat savory (HFSV), low fat savory (LFSV), high fat sweet (HFSW), low fat sweet (LFSW) sets, as shown in Table 8.

TABLE 8

| HFSV | LFSV | HFSW | LFSW |
|---|---|---|---|
| flora | bread | Cookies | Jelly Babies |
| salami | turkey | Chocolate Mousse | Fruit Cocktail |
| cheese | snack a jacks | | |
| crisps | cucumber | | |

A four way within-subjects ANOVA was performed with taste (savory/sweet), fat (high/low), inulin fiber (present/not) and ZOTRIM (present/not) as within-subjects factors. Significant main effects of taste (F (1,57)=10.457, p=0.002), fat (F (1,57)=90.637, p<0.001), inulin fiber (F (1,57)=9.775, p=0.003) and ZOTRIM (F (1,57)=23.944, p<0.001) were found on intake, but there were no significant interactions. Subsequent t-tests revealed that overall, gram intake of savory items was significantly greater than intake of sweet items (t (57)=3.234, p=0.002) and gram intake of low fat items was significantly greater than intake of high fat items (t (57)=9.520, p<0.001).

There was a significant reduction in HFSV intake with inulin fiber and ZOTRIM combined compared to placebo (t (57)=4.315, p<0.001) and compared to inulin fiber alone (t (57)=3.127, p=0.003). For LFSV intake, there was a significant reduction with ZOTRIM alone (t (57)=2.593, p=0.012) and with the ZOTRIM and inulin fiber combination (t (57)=2.470, p=0.017) compared to placebo. Intake of LFSV items was also significantly reduced following ZOTRIM alone (t (57)=2.004, p=0.050) and ZOTRIM+inulin fiber combined (t (57)=2.036, p=0.046) compared to inulin fiber alone.

It was also found that gram intake of HFSW items was significantly reduced with ZOTRIM alone (t (57)=2.207, p=0.031) and with ZOTRIM+inulin fiber combined (t (57)= 5.099, p<0.001) compared to placebo. HFSW intake was also significantly lower with ZOTRIM+inulin fiber combined versus with ZOTRIM alone (t (57)=2.440, p=0.018) or inulin fiber alone (t (57)=3.146, p=0.003). No significant effects of ZOTRIM or inulin fiber were found on gram intake of LFSW items.

Total Daily Intake. Total daily intake, including calories from the product, breakfast and lunch was analyzed using a 2×2 repeated measures ANOVA. This demonstrated a main effect of ZOTRIM on kcal intake (F (1,57)=16.681, p<0.001). There was no effect of inulin fiber (F (1, 57)=1.880, p=0.176) and no interaction between inulin fiber and ZOTRIM (F (1,57),=0.193, p=0.662). Paired t-tests revealed that there was a significant reduction in kcal intake with ZOTRIM alone (t (57)=3.365, p=0.001) and with the inulin fiber and ZOTRIM combination (t (57)=4.238, p<0.001) compared to placebo. It was also found that the kcal intake after ZOTRIM alone (t (57)=2.417, p=0.019) and after the combination of inulin fiber and ZOTRIM (t (57)= 3.178, p=0.002) was less than with inulin fiber alone.

Appetite. Subjective parameters (hunger, gastric fullness, satisfaction, desire to eat, prospective consumption, thirst and nausea) rated on VAS were analyzed using within-subject ANOVA for repeated measures with condition and time as within-subjects factors. Main effects of time were observed, as expected, reflecting changes in appetite ratings during the study days. Trends for main effects of hunger and desire to eat were observed as well as a main effect for nausea.

Trend for a main effect of ZOTRIM on hunger ratings (F(1, 56)=2.865, p=0.096). T-tests were used to investigate where the significant differences lay and showed that compared to the control condition a significant reduction in ratings of hunger was found in the ZOTRIM and inulin fiber combined condition at the pre lunch time point, (t(57) =2.071, p=0.043), mean values: 61.02 mm versus 54.41 mm respectively). Furthermore, compared to the inulin fiber only condition a significant reduction in ratings of hunger was found in the ZOTRIM and inulin fiber combined condition at the post lunch time point, (t(57)=2.770, p=0.008, mean values: 7.73 mm and 4.71 mm respectively).

Trend for an interaction between fiber and time on desire to eat (F(8, 456)=1.870, p=0.063). T-tests were used to investigate where the significant differences lay and showed that, compared to the control condition, a significant reduction in ratings of desire to eat was found in the ZOTRIM and inulin fiber combined condition at the pre dose lunch time point, (t(57)=2.302, p=0.025, mean values=: 58.84 mm versus 51.29 mm respectively). Furthermore, compared to the control condition a significant reduction in ratings of desire to eat was found in the inulin fiber only condition at the pre lunch time point, (t(57)=2.011, p=0.049, mean values: 61.19 mm versus 55.26 mm respectively). Moreover, compared to the control condition a significant reduction in ratings of desire to eat was found in the ZOTRIM and inulin fiber combined condition at the pre lunch time point, (t(57)= 2.230, p=0.030, mean values: 61.19 mm versus 53.86 mm respectively).

Significant main effect of fiber on nausea (F(1, 55)=6.203, p=0.016). T-tests were used to investigate where the significant differences lay and showed that compared to the control condition a significant reduction in ratings of nausea was found in the inulin fiber only condition 2 hours after breakfast time point, (t(57)=2.390, p=0.020, mean values: 9.50 mm versus 5.69 mm respectively). Furthermore, compared to the ZOTRIM only condition there was a significant reduction in nausea in the inulin fiber only condition at the 2 hours after breakfast time point, (t(57)=2.584, p=0.012, mean values: 10.03 mm versus 5.69 mm respectively). Furthermore, compared to the ZOTRIM and inulin combined condition there was a significant reduction in the inulin fiber only condition in ratings of nausea at the 2 hours after breakfast time point, (t(57)=2.053, p=0.045, mean values: 7.60 mm versus 5.69 mm respectively). Moreover, compared to the ZOTRIM only condition there was a significant reduction in ratings of nausea in the inulin fiber only condition at the pre dose lunch time point, (t(57)=2.040, p=0.046, mean values: 8.88 mm versus 5.97 mm respectively). In addition, compared to the ZOTRIM only condition there was a significant reduction in ratings of nausea in ZOTRIM and inulin fiber combined at the pre dose lunch time point, (t(57)=2.407, p=0.019, mean values: 8.88 mm versus 6.00 mm respectively).

Example 3: Animal Model for Food Intake

Studies are conducted with male Sprague-Dawley rats weighing 270-290 grams. Three days before the start of an experiment, the animals are weighed and individually housed. Normal rat chow pellets and tap water are present ad libitum and are provided by food troughs and drinking spouts, which allow continuous recording of the food consumed. Compositions containing plant extracts+inulin are administered at predetermined times to the treatment group. Food intake is recorded by continuously weighing the amount of food remaining in a round stainless steel food basket. Food intake is continuously or intermittently recorded over the entire time of an experiment. The weight of each animal is determined on each day of the experiment and recorded, together with any unusual observations, e.g., stressed animals, difficulties with plant extract application, etc. Statistical analysis to detect differences in ingestive behaviour between the control group and the treatment group is performed.

What is claimed is:

1. A composition for suppressing appetite comprising
   (a) about 150 to 450 mg of yerba maté leaf extract,
   (b) about 150 to 360 mg of guarana seed extract,
   (c) about 60 to 150 mg of damiana leaf extract, and
   (d) about 2 to 10 grams of isolated, fermentable inulin,
   wherein the composition is in a dosage form which provides for significantly lower food and calorie intake compared to:
   (i) the combination of (a), (b) and (c), and
   (ii) isolated, fermentable inulin alone.

2. The composition of claim 1, wherein said composition is formulated as a sachet, solid food product, dairy product, breakfast cereal, muesli, candy, confectionary, cookie, biscuit, cracker, chocolate, chew, chewing gum, dessert, powdered drink or liquid comestible.

* * * * *